(12) United States Patent
Toller et al.

(10) Patent No.: US 7,775,122 B1
(45) Date of Patent: Aug. 17, 2010

(54) TAPE OVERLAY FOR LASER BOND INSPECTION

(75) Inventors: Steven M. Toller, Dublin, OH (US); David W. Sokol, Dublin, OH (US); Craig T. Walters, Powell, OH (US)

(73) Assignee: LSP Technologies, Inc., Dublin, OH (US)

( * ) Notice: Subject to any disclaimer, the term of this patent is extended or adjusted under 35 U.S.C. 154(b) by 138 days.

(21) Appl. No.: 11/873,705

(22) Filed: Oct. 17, 2007

(51) Int. Cl.
*G01N 3/08* (2006.01)
(52) U.S. Cl. .......................................... 73/827; 73/760
(58) Field of Classification Search ............ 73/760–860
See application file for complete search history.

(56) References Cited

U.S. PATENT DOCUMENTS

| | | | | |
|---|---|---|---|---|
| 4,341,443 A | * | 7/1982 | Robinson | 359/519 |
| 4,544,181 A | * | 10/1985 | Maurer et al. | 283/74 |
| 5,702,565 A | * | 12/1997 | Wu et al. | 264/400 |
| 6,848,321 B2 | * | 2/2005 | Bossi et al. | 73/842 |
| 6,905,337 B1 | * | 6/2005 | Sachdeva | 433/229 |
| 7,264,536 B2 | * | 9/2007 | Wiswesser et al. | 451/6 |
| 7,509,876 B1 | * | 3/2009 | Sokol et al. | 73/827 |
| 7,556,387 B2 | * | 7/2009 | Moreau | 359/530 |
| 2002/0043109 A1 | * | 4/2002 | Siu | 73/643 |

OTHER PUBLICATIONS

Sokol et al., Laser System and Method for Non-Destructive Bond Detection and Evaluation, U.S. Appl. No. 10/950,865, filed Sep. 27, 2004.
Walters, Craig T., Apparatus and Method for Non-Destructive Testing, U.S. Appl. No. 11/227,745, filed Sep. 15, 2005.
Sokol et al., Laser Bond Inspection Using Annular Laser Beam, U.S. Appl. No. 11/873,677, filed Oct. 17, 2007.
Sokol et al., Lamb Waves for Laser Bond Inspection, U.S. Appl. No. 11/873,571, filed Oct. 17, 2007.

* cited by examiner

*Primary Examiner*—Max Noori
(74) *Attorney, Agent, or Firm*—Benjamen E. Kern

(57) ABSTRACT

Tape overlays for use in laser bond inspection are provided, as well as laser bond inspection systems and methods utilizing tape overlays.

23 Claims, 5 Drawing Sheets

TAPE OVERLAY FOR LASER BOND INSPECTION

BACKGROUND

Non-destructive inspection (NDI) of composite structures assembled with adhesive bonds is a need in, among other industries, the aircraft industry. Among other techniques, laser bond inspection (LBI) has proven useful. Normally, LBI involves deposition of laser energy onto the front surface of a bonded article, generating compression waves that reflect off of the back surface of the bonded article as tensile waves, the tensile waves predominantly providing the stresses that interrogate the bond. However, in a number of tasks, final paste bonds are not easily inspected by conventional LBI. For example, conventional LBI may be impractical in the inspection of aircraft closeout structures because the composite structure to be lased may be at least partially enclosed.

LBI employs stress wave generation principles similar to those used in laser shock processing. Laser shock processing assemblies and methods are described in U.S. Pat. Nos. 5,741,559, 5,911,891, 6,412,331, and 5,131,957, each of which is incorporated by reference herein in its entirety. However, each of these assemblies and methods involves the use of a tamping fluid over the article to be processed. More particularly, a substantially opaque layer covers the surface of the article to be processed. The substantially opaque layer may be, for example, tape or paint. The substantially opaque layer is then covered by a substantially transparent layer. The substantially transparent layer is typically water. However, as indicated above, many NDI tasks involve, for example, enclosed structures, and, thus, the use of a tamping fluid is not desirable, practical, or possible.

SUMMARY

In one embodiment, a system is provided for interrogating a bond in a bonded article, the system comprising: a tape overlay suitable for placement on the bonded article, the tape overlay comprised of a substantially opaque layer covered by a substantially transparent layer; a laser source configured to deposit laser energy onto the tape overlay, inducing a stress wave in the bonded article; and a surface motion detector.

In another embodiment, a system is provided for laser bond inspection, the system comprising: a laminate suitable to be adhered to a bonded article, the laminate comprising a substantially opaque layer; a substantially transparent layer covering the substantially opaque layer; and a retro-reflective material disposed on the substantially transparent layer, and wherein at least the substantially transparent layer is scored, cut, or slit into sections.

In yet another embodiment, a system is provided for laser bond inspection, the system comprising: a laser; a laminate configured to be adhered to a bonded article, the laminate comprising a substantially opaque layer covered by a substantially transparent layer and having a retro-reflective material disposed on the substantially transparent layer, and wherein the laminate is at least partially scored, cut, or slit; wherein the laser is capable of selectively directing an annular laser beam onto the laminate, the annular laser beam having an adjustable outer diameter and inner diameter, and wherein substantially no laser energy is directed within the inner diameter and substantially no laser energy is directed outside the outer diameter; and a surface motion detector.

In still another embodiment, a method for interrogating a bond in a bonded article is provided, the method comprising: positioning a laser source near the bonded article; placing a tape overlay over a portion of the bonded article to be lased, the tape overlay comprising an opaque layer covered by a transparent layer and having a retro-reflective material disposed on the tape overlay; depositing laser energy onto the tape overlay; and detecting bond failure.

In one embodiment, a tape overlay for use in laser bond inspection is provided, comprising: a substantially opaque layer capable of adhering to the surface of a bonded article; a substantially transparent layer adhered to the substantially opaque layer; and a retro-reflective layer adhered to the substantially transparent layer, the retro-reflective layer having an area smaller than the substantially transparent layer and the substantially opaque layer, and being positioned on the tape overlay; wherein the retro-reflective layer is configured to indicate surface motion in the bonded article when placed in operable communication with a surface motion detector.

BRIEF DESCRIPTION OF THE DRAWINGS

The accompanying figures, which are incorporated in and constitute a part of the specification, illustrate various example systems, methods, results, and so on, and are used merely to illustrate various example embodiments. It should be noted that various components depicted in the figures may not be drawn to scale, and that the various tape overlay scoring designs, number of sections, and tape overlay shapes (e.g., circular, square, etc.) depicted in the figures are presented for purposes of illustration only, and should not be considered in any way as limiting.

DETAILED DESCRIPTION

Figure 1:
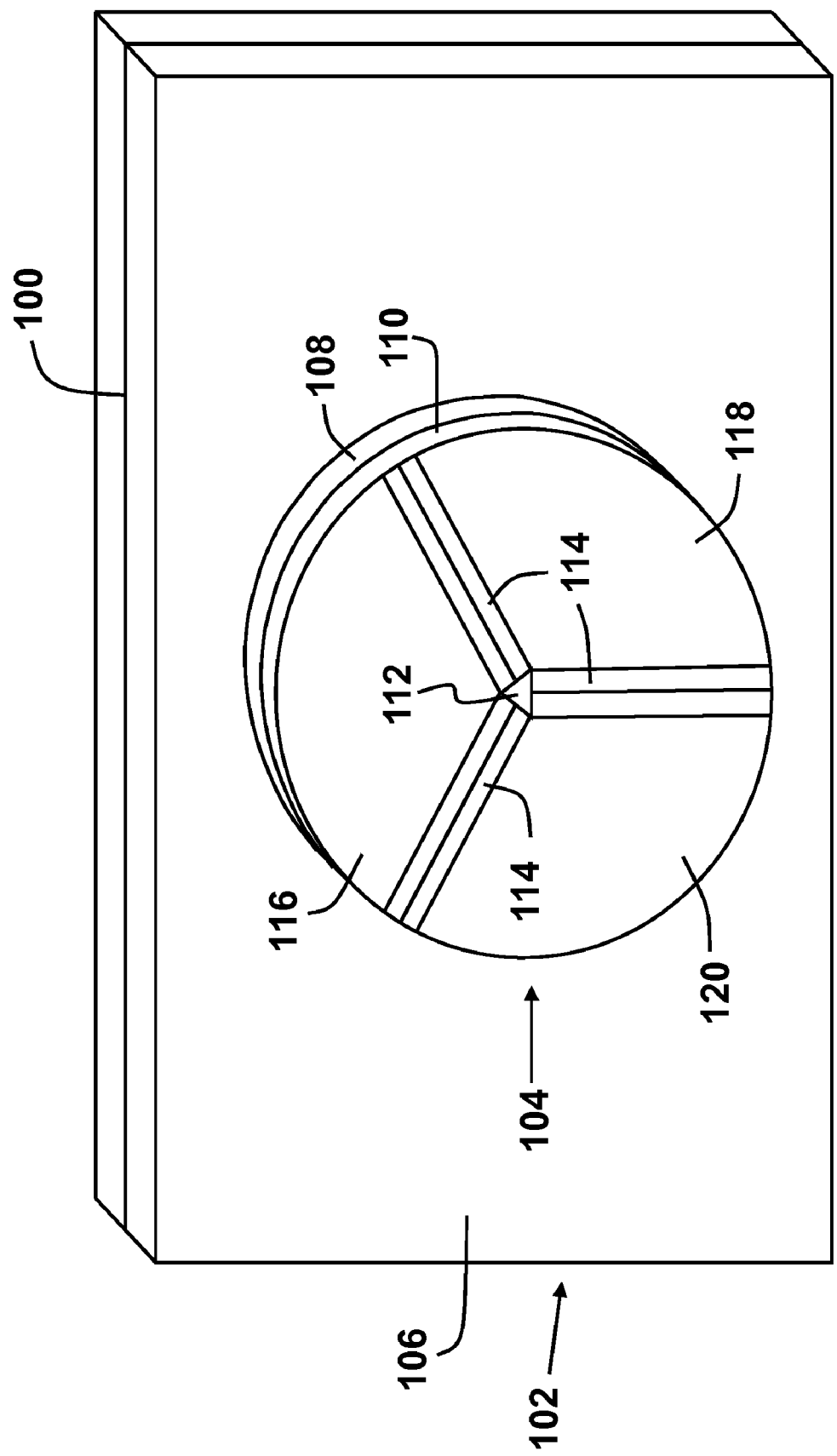
FIG. 1 illustrates an exemplary embodiment of a tape overlay system employing three processing sections.

The present embodiments disclose exemplary embodiments of tape overlays, also referred to as laminates or "inspection stickers," for use in laser bond inspection, and exemplary embodiments of laser bond inspection systems and methods utilizing tape overlays. The present embodiments will find use in any field in which non-destructive bond inspection is required or desired. The present embodiments will also find use when the use of tamping fluid in laser bond inspection is undesirable, impractical, or impossible.

In one embodiment, a system is provided for interrogating a bond in a bonded article, the system comprising: a tape overlay suitable for placement on the bonded article, the tape overlay comprised of a substantially opaque layer covered by a substantially transparent layer; a laser source configured to deposit laser energy onto the tape overlay, inducing a stress wave in the bonded article; and a surface motion detector. In one embodiment, the tape overlay may further comprise a retro-reflective material disposed on the tape overlay. The tape overlay may be circular, square, rectangular, or any other shape within the ambit of those skilled in the art. In one embodiment, the tape overlay may be substantially scored, cut, or slit into more than one section. For example, the tape overlay may be scored, cut, or slit into three sections. Of course, the tape overlay may be scored, cut, or slit into any number of sections or partial sections exceeding three sections.

In one embodiment, the laser source may be further configured to employ three laser pulses comprising a first low fluence pulse, a high fluence pulse, and a second low fluence pulse. In one embodiment, the first low fluence pulse is directed to a first of the three sections, the high fluence pulse is directed to a second of the three sections, and the second low fluence pulse is directed to a third of the three sections. An adjustable mask may be used to select portions of an input beam to direct the three pulses in sequence to the respective sections. Alternatively, an optical beam director may be used to point the entire beam to each of the three sections in sequence. The substantially opaque layer may be, for example, adhesive backed black coated aluminum tape or adhesive backed aluminum tape, or the substantially opaque layer may be any other suitable opaque material capable of being adhered. The substantially transparent layer may be, for example, optically transparent adhesive tape, or the substantially transparent layer may be any other suitable transparent material capable of being adhered.

In another embodiment, a system is provided for laser bond inspection, the system comprising: a laminate suitable to be adhered to a bonded article, the laminate comprising: a substantially opaque layer; a substantially transparent layer covering the substantially opaque layer; and a retro-reflective material disposed on the substantially transparent layer, wherein at least the substantially transparent layer is scored, cut, or slit into sections. The system may further comprise a laser source positioned near the bonded article. At least the substantially transparent layer may be scored, cut, or slit into three sections. The laser source may be configured to employ three laser pulses, comprising a first low fluence pulse, a high fluence pulse, and a second low fluence pulse. The first low fluence pulse may be directed to a first of the three sections, the high fluence pulse may be directed to a second of the three sections, and the second low fluence pulse may be directed to a third of the three sections. The system may further comprise a mask to direct the three pulses to the respective sections or, alternatively, the system may further comprise an optic to direct the three pulses to the respective sections. The opaque layer may be, for example, adhesive backed black coated aluminum tape or adhesive backed aluminum tape. The transparent layer may be, for example, clear tape.

The system may further comprise a surface motion detector. In one embodiment, the surface motion detector may be a laser interferometer, an electromagnetic acoustic transducer, a capacitance probe, or an ultrasonic transducer. In one embodiment, the surface motion detector may be a velocity interferometer for surfaces of any reflectance (VISAR).

FIG. 1 illustrates an exemplary embodiment of a tape overlay system employing three processing sections, for testing bond 100 of a bonded article 102. A tape overlay 104 may be disposed on a surface 106 of bonded article 102, tape overlay 104 being comprised of a layer of substantially opaque tape 108 covered by a layer of substantially transparent tape 110 (instead of flowing water). Tape overlay 104 may further comprise a retro-reflective material 112 on tape overlay 104. Retro-reflective material 112 may provide a means for process head alignment and surface motion detection via, for example, a VISAR probe. Retro-reflective material 112 may be for example, an adhesive backed, retro-reflective material known as Reflexite® (manufactured by Reflexite Corporation). Tape overlay 104 may be circular, as shown in FIG. 1, or it may be square, rectangular, or any other shape within the ambit of those skilled in the art. In one embodiment, tape overlay 104 may be scored, slit, or cut into more than one section, as shown at slits 114. As shown in FIG. 1, tape overlay 104 may be scored into three approximately equal sections.

In the depicted tri-sector configuration, bond 100 is interrogated by directing a laser beam to one of the three sectors. In one embodiment, the laser source may be configured to employ three laser pulses comprising a first low fluence pulse, a high fluence pulse, and a second low fluence pulse. In one embodiment, the first low fluence pulse is directed to a first of the three sections 116, the high fluence pulse is directed to a second of the three sections 118, and the second low fluence pulse is directed to a third of the three sections 120.

Figure 2:
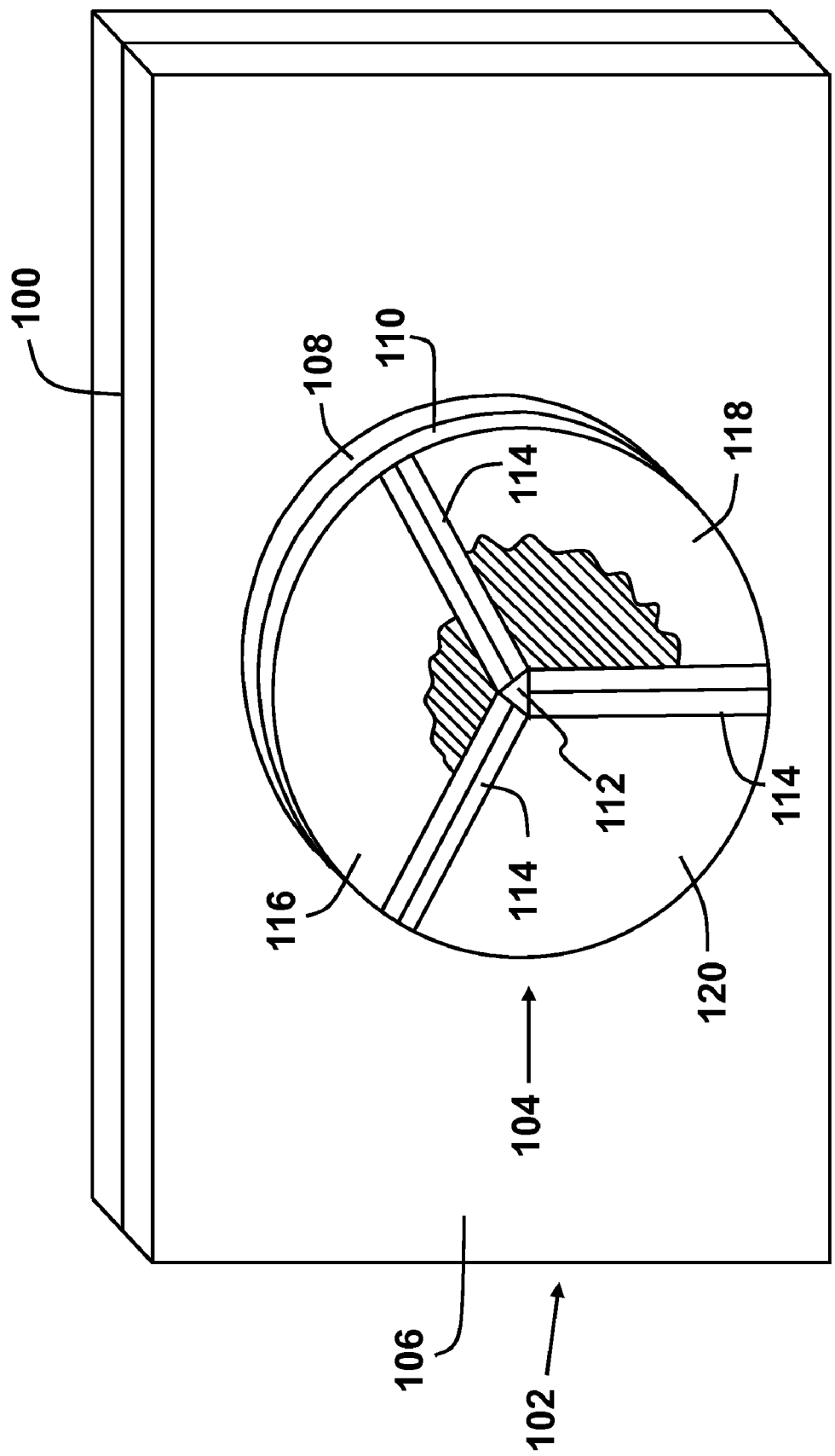
FIG. 2 illustrates an exemplary embodiment of a tape overlay system employing three processing sections, the tape overlay having been processed by a first low fluence pulse and a high fluence pulse according to a low-high-low fluence processing sequence.

FIG. 2 illustrates an exemplary embodiment of a tape overlay system employing three processing sections, the tape overlay 104 having been processed by a first low fluence pulse and a high fluence pulse according to a low-high-low fluence processing sequence. In one embodiment, the first low fluence pulse is directed to a first of the three sections 116 and the high fluence pulse is directed to a second of the three sections 118. As depicted, the third of the three sections, 120, has not been processed.

In one embodiment, each section of tape overlay 104 is separated by a slit 114 in tape overlay 104. As depicted in FIG. 2, scoring tape overlay 104 prevents damage in one sector from extending into an adjacent sector. The scoring also prevents "blow-off" of transparent tape 110 in one sector from lifting transparent tape 110 in an adjacent sector. Such slitting further may preserve the reflective center 112 of tape overlay 104 for VISAR inspection by not exposing reflective center 112 to any of the high or low fluence laser beams. It should be noted that, conventionally, a tamping fluid overlay would need to be reestablished after each pulse; however, in the present embodiments, clear tape may be used in place of tamping fluid as the transparent overlay.

In one embodiment, an exemplary suitable detector may be a VISAR probe. In one embodiment, the difference in the VISAR signatures for the two low-fluence pulses (in a low-high-low fluence pulse sequence) indicates whether the high fluence pulse broke the bond. The present embodiments may allow for an improved VISAR signal and, thus, a more accurate determination of the existence and extent of bond failure.

In an alternative embodiment, the laser source may be capable of depositing an annular laser beam onto the tape overlay, the annular laser beam having an outer diameter and an inner diameter, wherein the ratio of the outer diameter to the inner diameter is adjustable, and wherein at least some laser energy is contained between the outer diameter and the inner diameter. The laser source may be activated to generate alternating compression and tension waves that produce regions of tensile stress. The ratio of the outer diameter to the inner diameter may be adjusted to concentrate the tensile stress at a selected location within the bonded article. In one embodiment, the laser source may be activated in a single interrogation pulse. In another embodiment, the tape overlay may be scored, cut, or slit. The tape overlay may further comprise a retro-reflective material on the tape overlay. The area of the retro-reflective material may be less than or equal to the area defined by the inner diameter of the annular laser beam. In one embodiment, the area of the retro-reflective material may be sized such that the retro-reflective material is not directly subjected to the laser energy. The tape overlay may further comprise a tube having an internal area greater than or equal to the area of the retro-reflective material, but less than the area defined by the inner diameter of the annular laser beam, the tube extending perpendicularly from the tape overlay.

In yet another embodiment, a system is provided for laser bond inspection, the system comprising: a laser; a laminate configured to be adhered to a bonded article, the laminate comprising a substantially opaque layer covered by a substantially transparent layer and having a retro-reflective material disposed on the substantially transparent layer, arid wherein the laminate is at least partially scored, cut, or slit; wherein the laser is capable of selectively directing an annular laser beam onto the laminate, the annular laser beam having an adjustable outer diameter and inner diameter, and wherein substantially no laser energy is directed within the inner diameter and substantially no laser energy is directed outside the outer diameter; and a surface motion detector.

In one embodiment, the laser source may be activated to generate alternating compression and tension waves that produce regions of tensile stress. The ratio of the outer diameter to the inner diameter may be adjusted to concentrate the tensile stress at a selected location within the bonded article. The laser source may be activated in a single interrogation pulse. The laminate may further comprise a retro-reflective material on the laminate. The area of the retro-reflective material may be less than or equal to the area defined by the inner diameter of the annular laser beam. In one embodiment, the area of the retro-reflective material may be small enough that the retro-reflective material is not directly subjected to the laser energy. The laminate may further comprise a tube having an internal area greater than or equal to the area of the retro-reflective material, but less than the inner diameter of the annular laser beam, the tube extending perpendicularly from the laminate about the retro-reflective material.

As noted previously, the present embodiments may be employed for an annular laser beam by using single interrogation pulse (SIP) LBI. In SIP, bond detection generally involves detecting characteristic break indicators in the surface motion signature. The VISAR reflector portion (i.e., the retro-reflective material) of the tape overlay or laminate may be located on the axis (the inner diameter) of the main beam exposure area. Since the annular beam does not contain energy in its inner diameter, the retro-reflector does not receive damaging fluences. Thus, a sensitive real-time indication of bond failure may be achieved because the bond failure should occur under the retro-reflecting area.

In one embodiment, the opaque layer may be, for example, adhesive backed black coated aluminum tape or adhesive backed aluminum tape. Such aluminum tapes may partially vaporize upon lasing. Patterns of slits on the transparent overlay may be used to control where the tape overlay first lifts and, therefore, control the direction of release of any aluminum vapor.

In still another embodiment, a method for interrogating a bond in a bonded article is provided, the method comprising: positioning a laser source near the bonded article; placing a tape overlay over a portion of the bonded article to be lased, the tape overlay comprising a substantially opaque layer covered by a substantially transparent layer and having a retro-reflective material disposed on the tape overlay; depositing laser energy onto the tape overlay; and detecting bond failure. Of course, one of ordinary skill in the art will readily recognize that the proximity and/or orientation of the laser source relative to the bonded article may vary, and may be any operable or workable range and/or displacement.

The method may further comprise scoring, cutting, or slitting the tape overlay. The scoring may comprise scoring into more than one section. The scoring, cutting, or slitting may comprise scoring into three sections. In one embodiment, the depositing may comprise lasing onto the tape overlay in three pulses, the three pulses comprising a first low fluence pulse, a high fluence pulse, and a second low fluence pulse. The lasing may further comprise directing the first low fluence pulse onto a first of the three sections, directing the high fluence pulse onto a second of the three sections, and directing the second low fluence pulse onto a third of the three sections. The method may further comprise placing an adjustable mask within or before the laser source to select portions of an input beam to direct the three pulses in sequence to the respective sections. Alternatively, an optical beam director may be used to point the entire beam to each of the three sections in sequence.

In one embodiment, the surface motion detecting may comprise detecting with a laser interferometer, an electromagnetic acoustic transducer, a capacitance probe, or an ultrasonic transducer. The detecting may comprise detecting with a VISAR probe.

In an alternative embodiment, the depositing may comprise depositing an annular laser beam onto the tape overlay, the annular laser beam having an outer diameter and an inner diameter, and wherein the outer diameter contains laser energy. The method may further comprise adjusting the ratio of the outer diameter to the inner diameter. The depositing may comprise generating alternating compression and tension waves that produce regions of tensile stress. The tensile stress may be concentrated at a selected location within the bonded article. In one embodiment, the depositing may comprise lasing in a single interrogation pulse. The method may further comprise extending a tube perpendicularly from the tape overlay, the tube having substantially the same or greater internal area than the area of the retro-reflective material.

Figure 3:
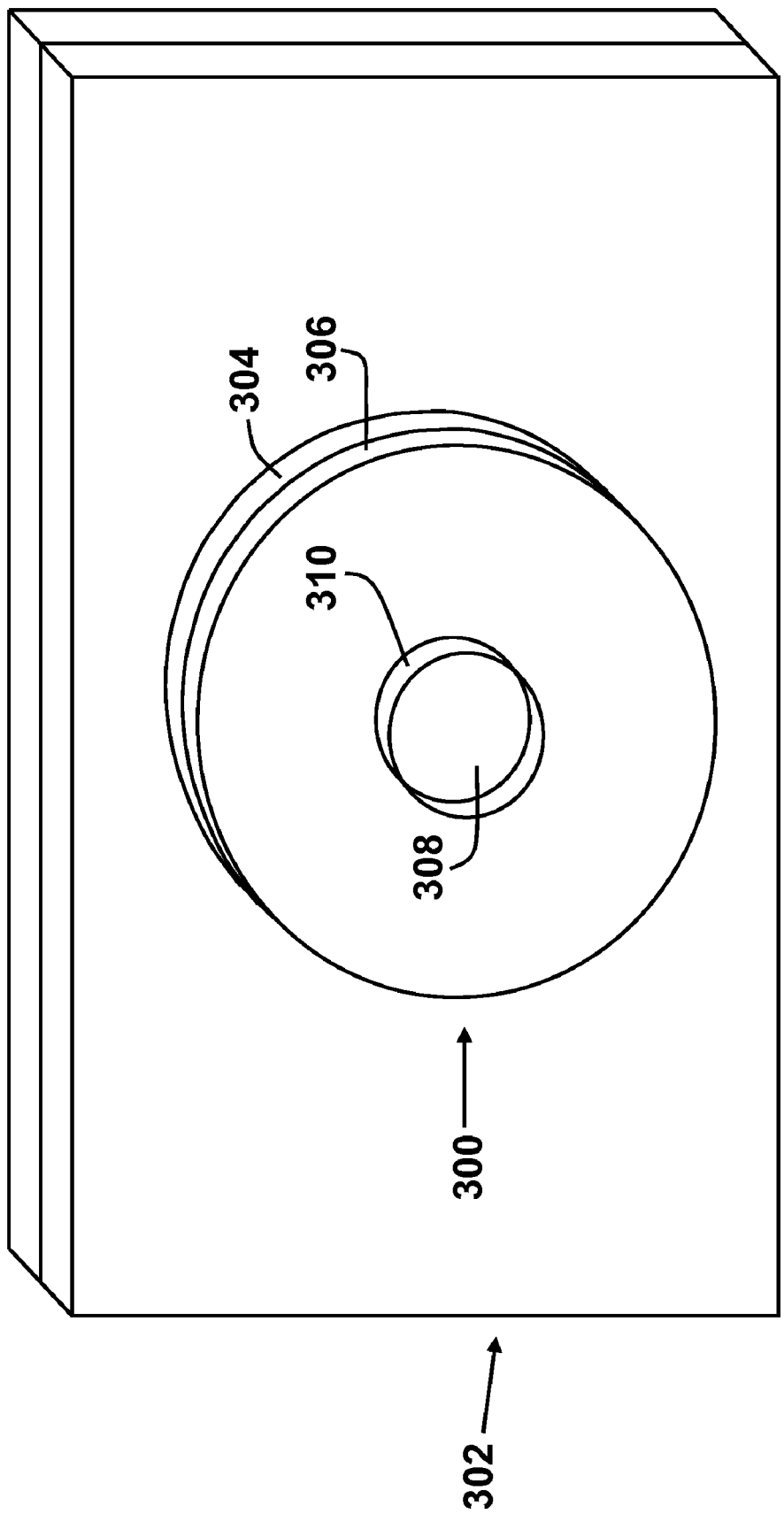
FIG. 3 illustrates an exemplary embodiment of a tape overlay system including a small tube for deflecting vapor.

FIG. 3 illustrates an exemplary embodiment of a tape overlay system including a small tube for deflecting vapor generated at the target surface by the laser beam. Thus, with reference to FIG. 3, tape overlay 300 may be disposed on bonded article 302, tape overlay 300 being comprised of an opaque layer 304, a transparent layer 306, and a retro-reflective material 308 on tape overlay 300. A small tube 310 may extend substantially perpendicularly from the surface of retro-reflective material 308, effectively deflecting vapor produced upon lasing and preventing absorbing deposits from degrading the retro-reflection.

In still another embodiment, a tape overlay is provided for use in laser bond inspection. The tape overlay comprises: a substantially opaque layer capable of adhering to the surface of a bonded article; a substantially transparent layer adhered to the opaque layer; and a retro-reflective layer adhered to the transparent layer, the retro-reflective layer having an area smaller than the transparent layer and the opaque layer, and being positioned substantially on the transparent layer; wherein the retro-reflective layer is configured to indicate surface motions in the bonded article when placed in operable communication with a surface motion detector. In one embodiment, the transparent layer may be scored, cut, or slit.

Unless specifically stated to the contrary, the numerical parameters set forth in the specification, including the attached claims, are approximations that may vary depending on the desired properties sought to be obtained according to the exemplary embodiments. At the very least, and not as an attempt to limit the application of the doctrine of equivalents to the scope of the claims, each numerical parameter should at least be construed in light of the number of reported significant digits and by applying ordinary rounding techniques.

The following examples are provided to illustrate various embodiments and shall not be considered as limiting in scope.

EXAMPLE 1

A three-segment tape overlay in accordance with FIG. 1 was exposed in a low-high-low (LHL) fluence sequence. A series of four inspection sticker exposures was conducted. Aluminum adhesive backed foil was used as the absorbing (opaque) layer, and transparent packing tape was used as the confining (transparent) layer. The diameter of the beam at the tape overlay was 14 mm. The high interrogating fluence ranged from 10 to 26 $J/cm^2$ (100 ns nominal pulse width). The material substrate was 20-ply/20-ply BMS 8-297 composite bonded with EA9394 paste adhesive after a sanded surface preparation. Each segment was exposed separately by rotating a mask in the unfocused beam.

Surface motions were detected by a VISAR probe. VISAR records for three of the exposures (where the interrogating pulse was 25.8 $J/cm^2$) showed that a front surface signal was acquired. Aluminum vapor produced during inspection using the three segment tape overlay did not interfere with the VISAR probe beam. The use of the mask reduced the laser fluence, because only a portion of each individual sticker section was exposed. Optics manipulation within the ambit of one skilled in the art may be desirable for some bonded articles, such as, for example, thick ($\geqq 1$ inch) bonded articles, to direct all of the available laser energy to the segment being processed.

Additional sticker geometries were explored to evaluate the front surface sensing concept. To simulate higher fluences that would be achieved on a tape overlay segment in an optimized design, circular spots of equivalent area to that used in the segmented sticker tests were employed in a series of exposures with a VISAR probe reflecting material adjacent to the circular spot.

Improved VISAR signals were achieved when using adhesive-backed, retro-reflective material (Reflexite®) in the probe location as opposed to bare aluminum. Reflexite® has the additional advantage of being tolerant of a probe VISAR beam that is off-normal incidence angle.

EXAMPLE 2

A series of single-pulse exposures was also conducted with the tape overlay structure according to FIG. 1. The tape overlay was applied to a coupon of 20-ply/20-ply BMS 8-297 composite bonded with EA9394 paste adhesive after a sanded surface preparation. The SIP technique involves only a single exposure and, thus, indications of bond failure may be found in the VISAR signal associated with the interrogating pulse (real time sensing). VISAR records for three different singe pulse tests on three different stickers showed bond failure.

EXAMPLE 3

Two scoring patterns were also tested using an annular laser beam. The scoring patterns were varied to optimize control of where the tape lifts first upon lasing, the intent being to control the direction of release of the aluminum vapor.

Figure 4:
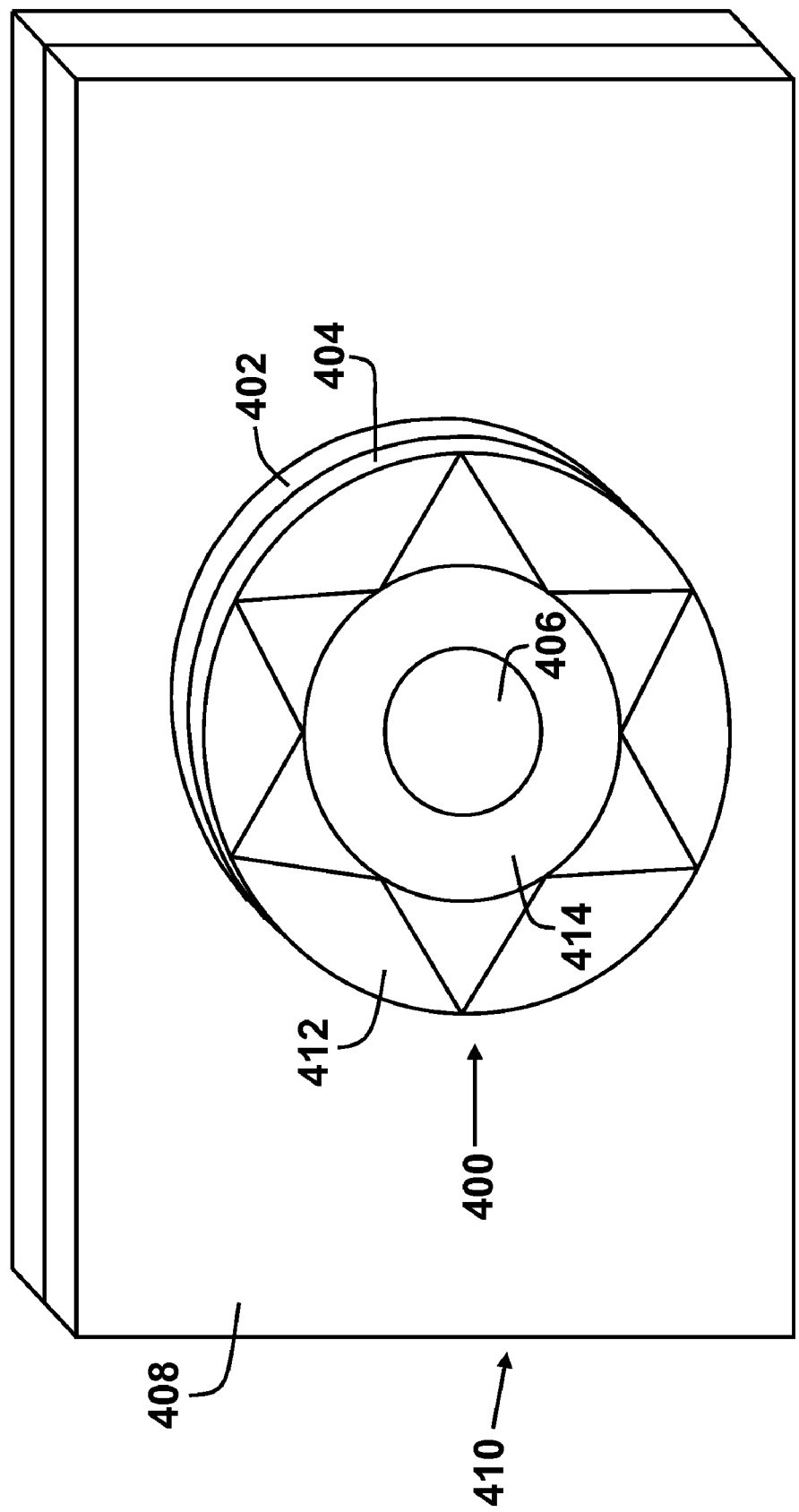
FIG. 4 illustrates an exemplary embodiment of a tape overlay pattern for use with an annular laser beam.

FIG. 4 illustrates an exemplary embodiment of a tape overlay pattern for use with an annular laser beam. In FIG. 4, a "star" pattern is depicted. Thus, with reference to FIG. 4, a tape overlay 400 comprising a substantially opaque overlay 402, a substantially transparent overlay 404, and a retro-reflective material 406 on tape overlay 400, is adhered to a surface 408 of bonded article 410. As shown in FIG. 4, an annular laser beam having an inner diameter and an outer diameter (the majority of the laser energy being contained within the two diameters) leaves an exposed area 412 and an unexposed area 414 on tape overlay 400, retro-reflective material 406 being within unexposed area 414.

Figure 5:
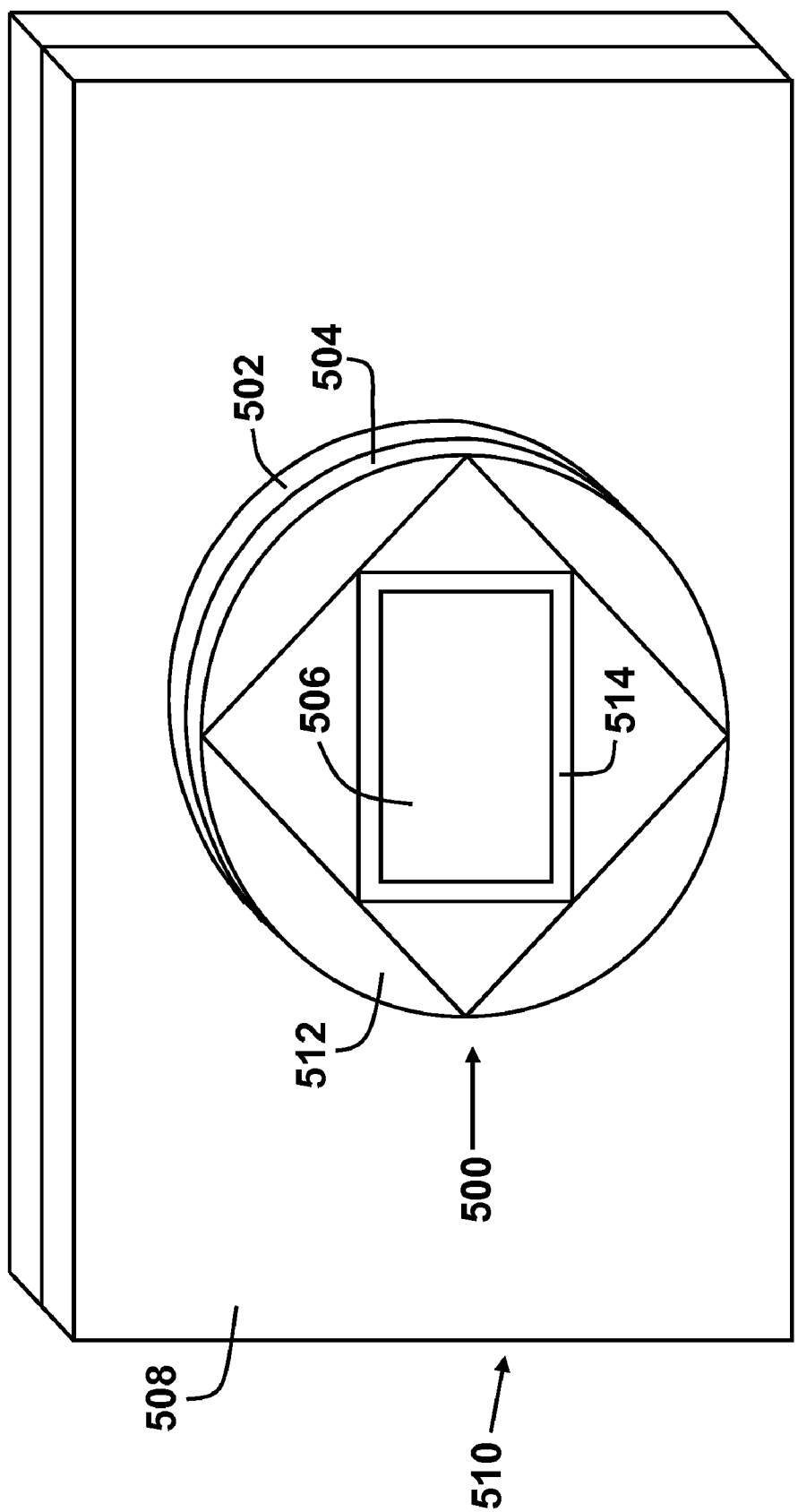
FIG. 5 illustrates an exemplary embodiment of a tape overlay pattern for use with an annular laser beam.

FIG. 5 illustrates another exemplary embodiment of a tape overlay pattern for use with an annular laser beam. In FIG. 5, linear barriers were used in a square pattern. Thus, with reference to FIG. 5, a tape overlay 500 comprising a substantially opaque overlay 502, a substantially transparent overlay 504, and a retro-reflective material 506 on tape overlay 500, is adhered to a surface 508 of bonded article 510. As shown in FIG. 5, an annular laser beam having an inner diameter and an outer diameter (the majority of the laser energy being contained between the two diameters) leaves an exposed area 512 and an unexposed area 514 on tape overlay 500, retro-reflective material 506 being within unexposed area 514.

In the star pattern, the tape points lifted first, and most of the vapor escaped radially outward. The star pattern had a larger main beam exposure area and created bond failure in the coupon, but vapor obscured about 80% of the VISAR beam in about 200-300 ns. The square pattern had less exposure area and did not cause a bond failure. However, the square pattern sticker limited the VISAR beam obscuration to about 50%. Vapor obscuration could be further reduced by using a small tube which projects from the surface of the reflector to deflect vapor.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Furthermore, while the systems, methods, and so on have been illustrated by describing examples, and while the examples have been described in considerable detail, it is not the intention of the applicant to restrict, or in any way, limit the scope of the appended claims to such detail. It is, of course, not possible to describe every conceivable combination of components or methodologies for purposes of describing the systems, methods, and so on provided herein. Additional advantages and modifications will readily appear to those skilled in the art. Therefore, the invention, in its broader aspects, is not limited to the specific details and illustrative examples shown and described. Accordingly, departures may be made from such details without departing from the spirit or scope of the applicant's general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

Finally, to the extent that the term "includes" or "including" or "having" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995).

What is claimed is:

1. A system for interrogating a bond in a bonded article, comprising:
a tape overlay suitable for placement on the bonded article, the tape overlay comprised of a substantially opaque layer at least partially covered by a substantially transparent layer;
a laser source configured to deposit laser energy onto the tape overlay, inducing a stress wave in the bonded article; and
a surface motion detector configured to detect surface motion in the bonded article caused by the stress wave.

2. The system of claim 1, wherein the tape overlay further comprises a retro-reflective material.

3. The system of claim 1, wherein the tape overlay is substantially scored, cut, or slit into more than one section.

4. The system of claim 3, wherein the laser source is further configured to employ three laser pulses comprising a first low fluence pulse, a high fluence pulse, and a second low fluence pulse.

5. The system of claim 4, wherein the tape overlay is slit into three sections and the first low fluence pulse is directed to a first of the three sections, the high fluence pulse is directed to a second of the three sections, and the second low fluence pulse is directed to a third of the three sections.

6. The system of claim 5, further comprising one or more of a mask and an optical beam director to direct the three laser pulses to the respective sections.

7. The system of claim 1, wherein the substantially opaque layer is adhesive backed black coated aluminum tape or adhesive backed aluminum tape, and wherein the substantially transparent layer is clear tape.

8. The system of claim 1, wherein the surface motion detector is at least one of a laser interferometer, an electromagnetic acoustic transducer, a capacitance probe, an ultrasonic transducer, and a velocity interferometer for surfaces of any reflectance (VISAR).

9. The system of claim 1, wherein the laser source is capable of depositing an annular laser beam onto the tape overlay, the annular laser beam having an outer diameter and an inner diameter, wherein a ratio of the outer diameter to the inner diameter is adjustable, and wherein at least some of the laser energy is contained between the outer diameter and the inner diameter.

10. The system of claim 9, wherein the laser source is activated in a single interrogation pulse.

11. The system of claim 9, wherein the tape overlay further comprises a retro-reflective material.

12. The system of claim 11, wherein the area of the retro-reflective material is less than or equal to the area defined by the inner diameter of the annular laser beam.

13. The system of claim 11, wherein the tape overlay further comprises a tube having an internal area greater than or equal to the area of the retro-reflective material, but less than the area defined by the inner diameter of the annular laser beam, the tube extending substantially perpendicularly from the tape overlay about the retro-reflective material.

14. A system for laser bond inspection, comprising:
a laminate suitable to be adhered to a bonded article, the laminate comprising:
a substantially opaque layer;
a substantially transparent layer covering the substantially opaque layer; and
a retro-reflective material disposed on the substantially transparent layer,
wherein at least the substantially transparent layer is scored, cut, or slit into sections.

15. The system of claim 14, further comprising a laser source positioned near the bonded article.

16. A system for laser bond inspection, comprising:
a laser;
a laminate configured to be adhered to a bonded article, the laminate comprising a substantially opaque layer, a substantially transparent layer, and a retro-reflective material, wherein the laminate is at least partially scored, cut, or slit;
wherein the laser is capable of selectively directing an annular laser beam onto the laminate, the annular laser beam having an adjustable outer diameter and inner diameter, and wherein substantially no laser energy is directed within the inner diameter and substantially no laser energy is directed outside the outer diameter.

17. The system of claim 16, wherein the laser generates tensile stress, and wherein the ratio of the outer diameter to the inner diameter is adjustable to concentrate the tensile stress at a location within the bonded article.

18. A method for interrogating a bond in a bonded article, comprising:
positioning a laser source near the bonded article;
placing a tape overlay over a portion of the bonded article to be lased, the tape overlay comprising an opaque layer, a transparent layer, and a retro-reflective material;
depositing laser energy onto the tape overlay; and
detecting bond failure.

19. The method of claim 18, further comprising scoring, cutting, or slitting the tape overlay.

20. The method of claim 18, further comprising scoring the tape overlay into three sections and directing a first low fluence pulse onto a first of the three sections, directing a high fluence pulse onto a second of the three sections, and directing a second low fluence pulse onto a third of the three sections.

21. The method of claim 20, further comprising placing a mask, an optic, or both, within or before the laser source to direct the three pulses to the respective sections.

22. The method of claim 18, wherein the detecting comprises detecting with at least one of a laser interferometer, an electromagnetic acoustic transducer, a capacitance probe, an ultrasonic transducer, and a velocity interferometer for surfaces of any reflectance (VISAR).

23. A tape overlay for use in laser bond inspection, comprising:
a substantially opaque layer capable of adhering to the surface of a bonded article;
a substantially transparent layer capable of adhering to the substantially opaque layer; and
a retro-reflective layer;
wherein the retro-reflective layer is configured to indicate surface motion in the bonded article when placed in operable communication with a surface motion detector.

* * * * *